Aug. 8, 1939. P. ECKE Plant Pat. 336
POINSETTIA
Filed Sept. 13, 1938
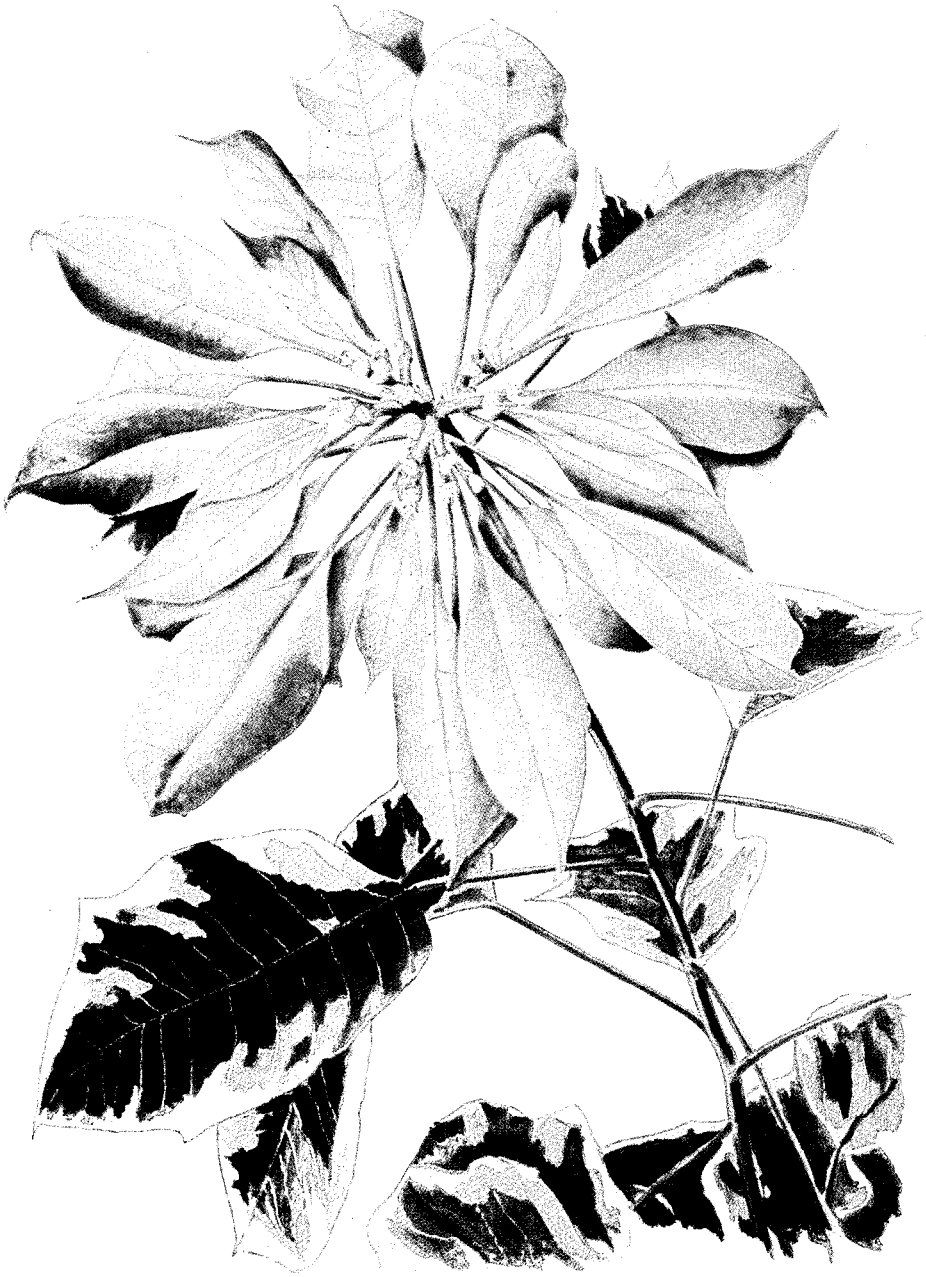
Inventor
Paul Ecke
By Robert Robb
attorneys Patented Aug. 8, 1939

Plant Pat. 336

UNITED STATES PATENT OFFICE

336

POINSETTIA

Paul Ecke, Encinitas, Calif.

Application September 13, 1938, Serial No. 229,760

1 Claim. (Cl. 47—60)

The present invention relates to a new and distinct variety of poinsettia, originating as a sport. In tracing back the origin, it is definitely known that the ancestors of the present discovery originated from a wild free-nature and insignificant shrub, known botanically by the name "*Euphorbia pulcherrima*", which was found in the wilds of the Republic of Mexico, and exported to the United States by General Joel Robert Poinsett, who at that time, was the first United States Minister to Mexico. Some of said plants were received by Robert Buist of Philadelphia, Pa., U. S. A,. who improved and further developed them, and named them "*Euphorbia poinsettia*", in honor of the said discoverer.

In the year of 1921 some of the poinsettia plants which had been known under the trade name "Oak Leaf poinsettia" were planted in my greenhouse at Encinitas, California.

In the summer of 1933 a sport of poinsettia (*Euphorbia pulcherrima*) was discovered by me on one of my poinsettias and asexually propagated. It has remained true to type, through the propagation of several thousand plants.

The colors herein mentioned correspond approximately with those shown and identified by the Robert Ridgway color standard and nomenclature, herein referred to by name and identified by the color name and plate of said color standard.

The accompanying painting, forming a part of this application, graphically shows the subject in its full maturity, which painting is a face view of the subject, showing it in its normal condition, with its grace and charm of appearance.

The following is a detailed description of the new variety:

*Structure*

The stems are long, stiff, and very strong, and are comparatively small in cross section. Their average length is four feet, with many small branches at the top, usually growing from three knob-like branches. Each branch bears several bracts and a few flowers.

*Petioles*

Extending outwardly from around each of the stems is a plurality of petioles, which are attached to and arranged spirally around their respective stems, with the inner or base portion spanning the interior of its respective stem; with their color similar to that of the stems, but more of a light "Terre Verte" color, shown on Plate XXXIII.

*Leaves*

The leaves are abundant, large and very attractive in appearance. They are ovate and very prominently pinnatifid, the latter being acuminate. Their color is variegated, having a mottled appearance on the upper side of the leaves, of a Grape Green (Plate XLI) with light portions of Sulphur Yellow (Plate V).

*Bracts*

The bracts are similar to the leaves, except that they are much smaller, are lanceolate in contour, do not protrude outwardly so far, and near their maturity they assume a color entirely different therefrom, which is that their upper or face sides are a "Jasper Red" as shown in Plate XIII and their under sides are a "Pale Salmon Color" as shown on Plate XIV.

*Flowers*

A node is formed on the upper end of each peduncle, each of which usually presents three short and comparatively large heavy stem-like knobs, which protrude upward and expansively apart, each of which latter carries a flower of a "Pale Greenish Yellow" color, corresponding to the color of the knobs and which is substantially as that shown on Plate V, but prior to maturity is almost white. Each of said flowers usually contains three ovules which, if properly impregnated, will germinate a new poinsettia. The nine to twelve flowers are very small and are surrounded by the bracts, and they are a "Pale Greenish Yellow" Plate V, which prior to maturity are almost white. Each flower usually develops three seeds and the seed pods are each about ¼-inch in diameter.

*Appearance*

When looking directly at the center of the bloom, that is, at the upper half of the painting, the leaves and bracts form the background of the flowers. Perhaps the most ornamental parts of this poinsettia are the colored bracts about a cluster of tiny flowers, which make an attractive combination.

*Thorns*

There is nothing of this nature in connection with this plant.

*Dimensions*

The total height of the plant at maturity is approximately eight feet, and the greatest lateral dimension is approximately five feet.

*Habits*

Vigorous, but slow in growth, easily cultivated, if properly handled, and persistent and perennial in growth.

*Immunity*

The entire plant seems to be immune from insects, disease, and all other obnoxious and detrimental interference.

*Aroma*

None apparent.

*Variations*

Each of the features mentioned regarding this plant is simply a replica of the same in all the others which I have produced; that is to say, there is very little, if any, difference in corresponding features. However, in comparison with the same grown in various localities, in different soil, and at various times of the year, in different temperature, or in different greenhouses, or in the open, and even by different persons, there may be some slight variations.

*Maintenance*

After being cut, the bloom and the foliage, with ample stem, and even without refrigeration, have the quality of keeping in excellent condition for a period of a week or ten days, depending upon the exterior conditions.

*Planting*

I have found by experience that if a cutting is taken and planted at any time from May until September, that the plant will mature in November, retaining its beauty for two months, after which it will remain dormant for about three months; however, the above estimate is subject to variations, depending on the climate and other conditions. It can be grown successfully anywhere in the United States and Canada in greenhouses kept at the proper temperature, but outdoors only in frost-free sections.

*Comparisons*

Compared with other species of poinsettias, the difference is principally that this new production presents foliage that is variegated and, therefore, more attractive than other species.

*Reproduction*

The reproduction of this new poinsettia is only by cuttings, which are usually four to five inches long. Propagation can be successfully continued at Encinitas, California, until early September.

Having now fully shown and described my new poinsettia, what I claim and desire to secure by Letters Patent of the United States is:

A new and distinct variety of poinsettia, characterized by the brightness of coloring of foliage and flowers and the variegated color and mottled appearance of the leaves, substantially as shown and described.

PAUL ECKE.